US00PP25399P2

(12) United States Plant Patent
Zwagerman

(10) Patent No.: US PP25,399 P2
(45) Date of Patent: Mar. 31, 2015

(54) ***HOSTA* PLANT NAMED 'SPARKLER'**

(50) Latin Name: ***Hosta* hybrid (Tratt.)**
Varietal Denomination: Sparkler

(71) Applicant: Hannah B. Zwagerman, Zeeland, MI (US)

(72) Inventor: Hannah B. Zwagerman, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 159 days.

(21) Appl. No.: 13/815,746

(22) Filed: Mar. 16, 2013

(51) Int. Cl.
*A01H 5/00* (2006.01)

(52) U.S. Cl.
USPC ..... Plt./353

(58) Field of Classification Search
CPC ..... A01H 5/02; A01H 5/12
USPC ..... Plt./353
See application file for complete search history.

(56) References Cited

PUBLICATIONS

*Hosta* 'Sparkler' PPAF. Walters Gardens, Inc. 2014 retrieved on Oct. 8, 2014, retrieved from the Internet at <http://www.waltersgardens.com/plants/Hosta/2211_HostaSparklerPPAF.aspx> 3 pp.*

Martin, Susan, Walters Gardens, Inc. Wholesale Catalog, Summer 2012-Spring 2013, pages front cover and p. 144, Walters Gardens Inc., Zeeland, MI USA.

Martin, Susan, Walters Gardens, Inc. Wholesale Catalog, Summer 2013-Spring 2014, pages front cover and p. 140, Walters Gardens Inc., Zeeland, MI USA.

* cited by examiner

*Primary Examiner* — June Hwu

(57) ABSTRACT

A new and distinct *Hosta* plant named 'Sparkler', characterized by stiff, heavy-substance, thick foliage with conduplicate leaf blades with variegation of white centers and dark green margins and intermediate colors feathered between margin and center. *Hosta* 'Sparkler' flowers with erect cream-colored scapes having upright facing light lavender flowers in mid-July subtended by variegated bracts on a compact plant.

2 Drawing Sheets

Botanical classification: *Hosta* hybrid (Tratt.).
Variety denomination: 'Sparkler'.

BACKGROUND OF THE INVENTION

The present invention relates to the new and distinct cultivar of *Hosta*, botanically known as *Hosta* hybrid (Tratt.), and hereinafter referred to as the cultivar 'Sparkler'. The new plant was discovered by the inventor, Hannah B. Zwagerman as a non-induced, naturally-occurring whole-plant mutation of *Hosta* 'Fireworks' U.S. Plant Pat. No. 16,062 in a greenhouse at a nursery in Zeeland, Mich., USA during the summer of 2007. Asexual propagation of the plant at the same nursery by tissue culture and division has shown that the unique and distinct characteristics of this new plant are stable and reproduce true to type in successive generations.

SUMMARY OF THE INVENTION

*Hosta* 'Sparkler' is unique from its mutation parent, *Hosta* 'Fireworks', and all other *Hosta* cultivars known to the inventor, in several traits. *Hosta* 'Fireworks' is the nearest comparison variety known to the inventor. *Hosta* 'Fireworks' is a tissue-culture derived mutation from *Hosta* 'Loyalist' (not patented), which is a mutation of *Hosta* 'Patriot' (not patented) which originated as a mutation from *Hosta* 'Francee' (not patented). *Hosta* 'Francee' and 'Patriot' both have creamy white margins with the former having a thinner margin, and the latter, wider margins. *Hosta* 'Loyalist' (a reverse-type variegation pattern with creamy white centers and green margins) has a broader and flatter leave blade than either 'Fireworks' or the new plant.

Several other named cultivars are indistinguishable or similar to *Hosta* 'Loyalist' including: 'Fire and Ice' (not patented), 'Mademoiselle' (not patented), 'Pathfinder' (not patented), 'Paul Revere' (not patented) and 'Snowdrift' (not patented). *Hosta* 'Fireworks' has a narrower leaf, with a folded blade. In side by side comparisons 'Sparkler' is a more rapid grower than both 'Loyalist' and 'Fireworks', but in size 'Sparkler' is smaller and more compact in plant height and width than both 'Loyalist' and 'Fireworks'. 'Sparkler' reaches saleable size in an 8 cm diameter plug in about 5 months from a rooted tissue culture plantlet. *Hosta* 'Sparkler' has very thick, rigid leaves giving the whole plant an upright form and habit. The leaf blades and petioles have a wide dark green margin and creamy-white centers. 'Sparkler' flowers in mid-summer with light lavender flowers, on scapes above the foliage. Other similar *Hosta* cultivars include 'Little Treasure' U.S. Plant Pat. No. 21,210, which has flatter more elongated leaf blades, more acute leaf apex, a more glaucous texture giving the foliage a bluer margin than 'Sparkler' and the leaf center of 'Little Treasure' is more yellowish creamy colored.

*Hosta* 'Sparkler' is unique from all other known *Hosta* cultivars in the combined characteristics:

1. Stiff, heavy-substance, thick foliage with conduplicate leaf blades.
2. Variegation of white centers and dark green margins and intermediate colors feathered between margin and center.
3. Erect cream-colored scapes with upright facing light lavender flowers in mid-July and each flower subtended by a variegated bract.
4. Short habit with dense rhizomes

BRIEF DESCRIPTION OF THE DRAWINGS

The photographs of the new invention demonstrate the overall appearance of the plant including the unique traits. The colors are as accurate as reasonably possible with color reproductions. Some slight variation of color may occur as a result of lighting quality, intensity, wavelength, direction or reflection.

DETAILED BOTANICAL DESCRIPTION

Figure 1:
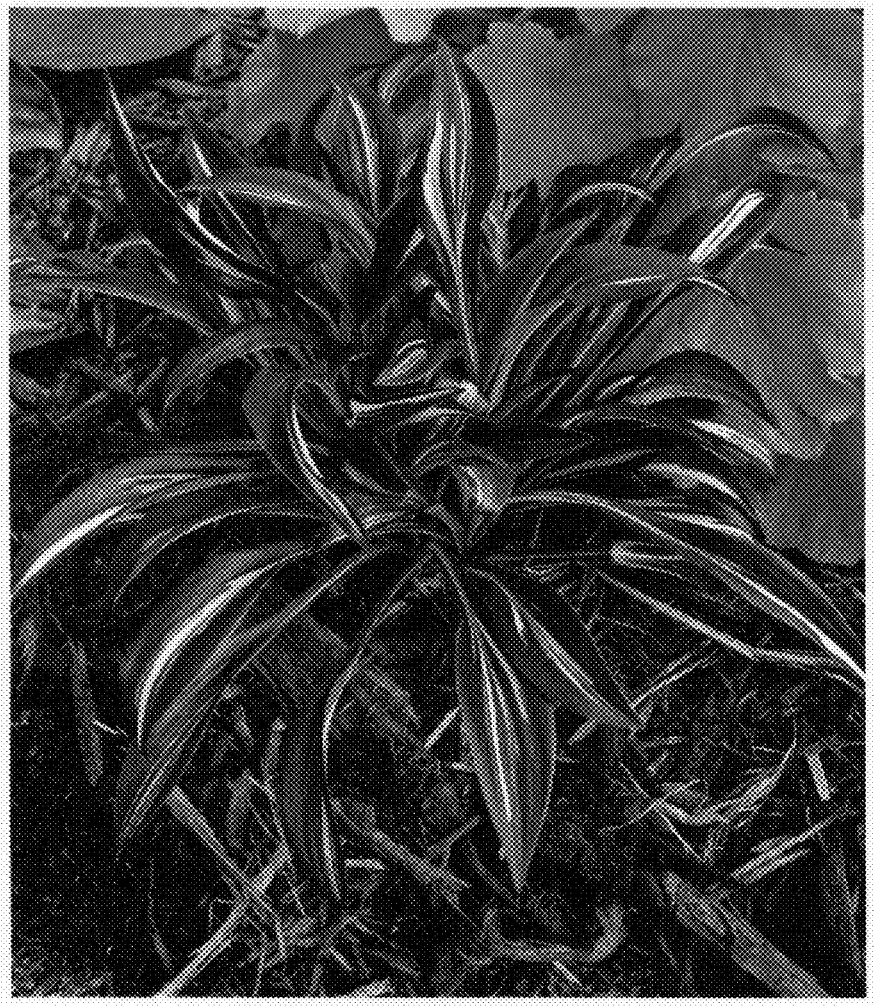
FIG. 1 shows a two-year old plant of *Hosta* 'Sparkler' in a trial garden in mid-season before flowering.
Figure 2:
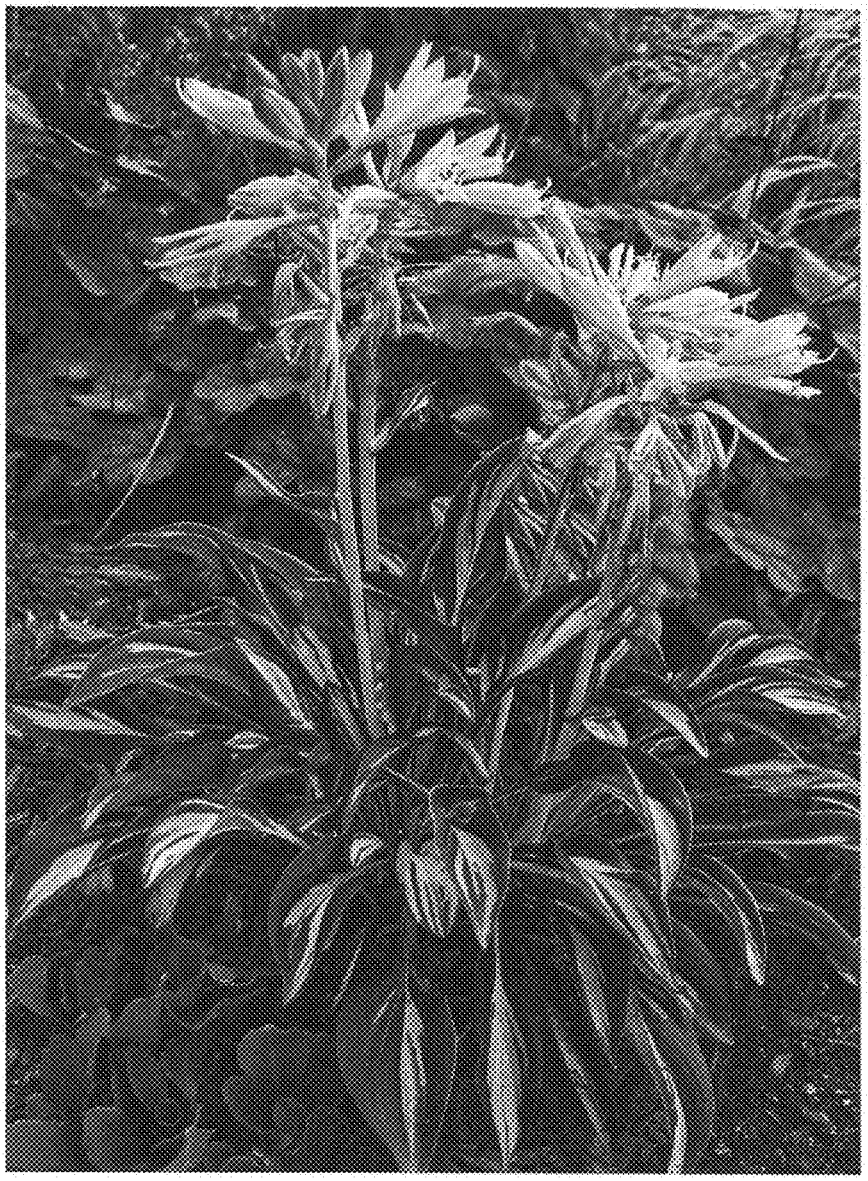
FIG. 2 shows a three-year old plant in flower.

The following descriptions and color references are based on The Royal Horticultural Society Colour Chart (2001 edition) except where common dictionary terms are used. The new plant, *Hosta* 'Sparkler', has not been observed under all possible environments. The phenotype may vary slightly with different environmental conditions, such as temperature, light, fertility and moisture, but without any change in the genotype.

The following observations and size descriptions are of a three-year old plant in a six-liter container grown in a greenhouse in Zeeland, Mich., USA under 50% artificial shade, day temperatures of 20 to 33 degrees C., and night temperatures of 15 to 25 degrees C.

Botanical classification: *Hosta* hybrid cultivar 'Sparkler'.

Parentage: Naturally-occurring whole-plant mutation of *Hosta* 'Fireworks' U.S. Plant Pat. No. 16,002.

Propagation: Method by tissue culture and division; time to initiate roots from both division and tissue culture about 21 to 24 days from cutting.

Rooting habit: Normal, fleshy, about 2.5 mm thick, lightly branching; root color normally lighter than RHS 155D.

Plant habit: Herbaceous, densely rhizomatous perennial, symmetrical with erect rarely arching peduncle, leaves upright and erect through flowering period, becoming more horizontal later in the season and in maturity.

Crop time: Under normal summer greenhouse growing conditions about 20 weeks to finish in a one-liter container; plant vigor good.

Plant size: Foliage at flowering is 15.0 to 20.0 cm tall above soil line and 35.0 to 40.0 cm wide at widest point about 5.0 to 10.0 cm above soil line; scape flowering to 37.0 cm tall.

Foliage description: Elliptic leaf blades with acute apex and attenuate base; stiff thick substance, entire, simple, glabrous, glossy above, slightly glaucous below; Leaf blades; conduplicate, 9.0 to 11.0 cm long and 3.2 to 4.2 cm wide average about 10.0 cm long and 3.5 cm wide; variegation of green margins and creamy white centers with intermediate colors feathered between; margin width variable between 6.0 mm and 12.0 mm at the widest point.

Foliage color: Emerging adaxial margin darker than RHS 144A and adaxial center between RHS 150D and RHS 154D with intermediate feathering of nearest RHS 147D and between RHS 144A and RHS 144B; emerging abaxial margin between RHS 138A and RHS 138B and abaxial center nearest RHS 13D with intermediate feathering between RHS 144A and RHS 144B; mid-season and later adaxial margin nearest RHS 139A and adaxial center nearest RHS 155D with intermediate feathering of lighter than RHS N138D, nearest RHS 143B and nearest RHS N138B; mid-season and later abaxial margin nearest RHS N138A and abaxial center nearest RHS 155D with intermediate feathering of nearest RHS 144A, nearest RHS N138C and nearest RHS 137C.

Venation: Parallel, at three-years old five to six vein pairs on either side of main center vein.

*Vein color*.—Same color as surrounding leaf surface either adaxial or abaxial.

Petioles: Entire, glabrous, glossy above and glaucous below; 6.0 to 9.5 cm long and 6.0 to 8.5 mm wide.

*Petiole color*.—Adaxial margin continues with leaf blade color of nearest RHS 139A on the margin and center nearest RHS 155D; abaxial margin nearest RHS N138A and center nearest RHS 155C.

Flower description:

*Buds*.—One to two days prior to opening — narrowly clavate, acute apex; upright in bud nearly adpressed along peduncle; 2.5 to 3.2 cm long, up to 1.0 cm wide.

*Bud color*.—Tepals between RHS 76A and RHS 76B with fissures between RHS N81B and N81C; apical 3.0 mm tips with green ridges of nearest RHS 137A.

*Flowers*.—27 to 35 per scape, usually one scape per division; funnelform, 2.0 to 2.5 cm wide and 3.0 to 3.5 cm long, (distal flowers being smaller) subtended by a single bract: flowers persist for a normal period, up to two days on or off the plant, and the scapes remain effective from mid-July to early August.

Flower fragrance: None detected.

Tepal: Normally six, simple, entire, fused at the base, oblong to elliptic, with slightly-recurved acute apex, approximately 3.5 cm long and 1.0 cm wide, arranged in two layers of three, the inner three with clear margin of about 1.0 to 2.0 mm wide.

*Tepal color*.—Distal main adaxial color in center of tepals is Red purple RHS 69D with violet stripes of RHS 84B, 2.0 to 3.0 mm margin of whiter than RHS 155D except clear transparent margin on inner tepal set; distal back of tepals between RHS 75B and 76B without obvious stripes.

Bract: Simple, entire, narrowly-acute, sessile, with base clasping scape, up to 4.0 cm long and 1.4 cm wide; persist beyond flowers dehiscence; with the same colors and pattern as the leaves.

Peduncle: Glaucous, erect to 38.0 cm tall and 5.0 mm in diameter; color nearest RHS 11D with of stippling lighter than RHS 187D concentrating heavier at the apical one third.

Pedicel: Approximately 8.0 mm long, 3.0 mm wide, color nearest RHS 145D with stippling of nearest RHS 76A.

Gynoecium:

*Style*.—Single, 3.5 to 4.0 cm long, 1.0 mm diameter curled upward at distal end; near white, lighter than RHS 155D.

*Stigma*.—Globose, up to 2.0 mm diameter; white, lighter than RHS 155D.

Androecium:

*Filaments*.—Normally six, slightly curved in middle and proximal ⅓; approximately 1 mm in diameter and up to 4.0 cm long; color white, lighter than RHS 155D.

*Anthers*.—About 3.5 mm long, 1.0 mm wide, color nearest about N187B around margin of abaxial side, nearest RHS 155D in center.

*Pollen*.—Spherical, less than 0.1 mm diameter; color yellow-orange nearest RHS 17B.

Seeds: Not yet observed.

Pest and disease resistance: The plant is more resistant to melting-out than many other white or light-centered cultivars. It grows best with plenty of moisture but is able to tolerate some drought. Hardiness to at least USDA zone 3, and other disease resistance is typical of other *Hostas*. 'Sparkler' appears more resistant to slugs and other pests than *Hostas* with *Hosta plantaginea* lineage.

I claim:

1. A new and distinct cultivar of ornamental *Hosta* plant named 'Sparkler' as herein described and illustrated, suitable as a potted plant, patio planters, for landscaping as a specimen or en masse, and for fresh-cut arrangements.

* * * * *